United States Patent
Bleam et al.

(10) Patent No.: US 6,887,263 B2
(45) Date of Patent: May 3, 2005

(54) VALVED CONNECTOR ASSEMBLY AND STERILITY BARRIERS FOR HEAT EXCHANGE CATHETERS AND OTHER CLOSED LOOP CATHETERS

(75) Inventors: Jefferey C. Bleam, Boulder Creek, CA (US); George Tsai, Sunnyvale, CA (US)

(73) Assignee: Radiant Medical, Inc., Redwood City, CA (US)

( * ) Notice: Subject to any disclaimer, the term of this patent is extended or adjusted under 35 U.S.C. 154(b) by 0 days.

(21) Appl. No.: 10/273,637

(22) Filed: Oct. 18, 2002

(65) Prior Publication Data

US 2004/0111138 A1 Jun. 10, 2004

(51) Int. Cl.[7] .................................................. A61F 7/00
(52) U.S. Cl. ....................................... 607/105; 607/106
(58) Field of Search ........................... 607/96, 104–106

(56) References Cited

U.S. PATENT DOCUMENTS

| | | |
|---|---|---|
| 4,327,723 A | 5/1982 | Frankhouser |
| 4,436,125 A | 3/1984 | Blenkush |
| 4,515,592 A | 5/1985 | Frankhouser |
| 4,834,709 A | 5/1989 | Banning et al. |
| 5,052,725 A | 10/1991 | Meyer et al. |
| 5,104,158 A | 4/1992 | Meyer et al. |
| 5,312,337 A | 5/1994 | Flaherty et al. |
| 5,704,106 A | 1/1998 | Sampson et al. |
| 5,715,815 A | 2/1998 | Lorenzen et al. |
| 5,799,987 A | 9/1998 | Sampson |
| 5,937,885 A | 8/1999 | Sampson |
| 6,146,411 A | 11/2000 | Noda et al. |
| 6,165,185 A | 12/2000 | Shennib et al. |
| 6,251,116 B1 | 6/2001 | Shennib et al. |
| 6,287,326 B1 | 9/2001 | Pecor |
| 6,440,158 B1 | 8/2002 | Saab |
| 6,458,140 B2 | 10/2002 | Akin et al. |

FOREIGN PATENT DOCUMENTS

WO  0238091  5/2002

*Primary Examiner*—Roy D. Gibson
(74) *Attorney, Agent, or Firm*—Robert D. Buyan; Stout, Uxa, Buyan & Mullins, LLP

(57) ABSTRACT

A connector assembly for catheters having closed loop flow circuits, such as some balloon catheters and heat exchange catheters. The connector assembly comprises first and second connector bodies that may be connected and disconnected from one another. When the connector bodies are disconnected, a syringe or negative pressure source may be attached to withdraw residual fluid from the catheter's closed loop circuit and to deflate any expandable portion of the closed loop circuit (e.g., balloon or expandable heat exchanger). A one way flow valve prevents make up air or other fluid from entering the catheter while the negative pressure is being applied. Also disclosed are sterility barrier assemblies for all types of catheters. Such sterility barrier assemblies are operative to prevent contamination of the portion of a catheter that remains outside of a patient's body so that the catheter may subsequently be further advanced into the patient's body without introducing microbes or other contaminants into the patient's body.

51 Claims, 8 Drawing Sheets

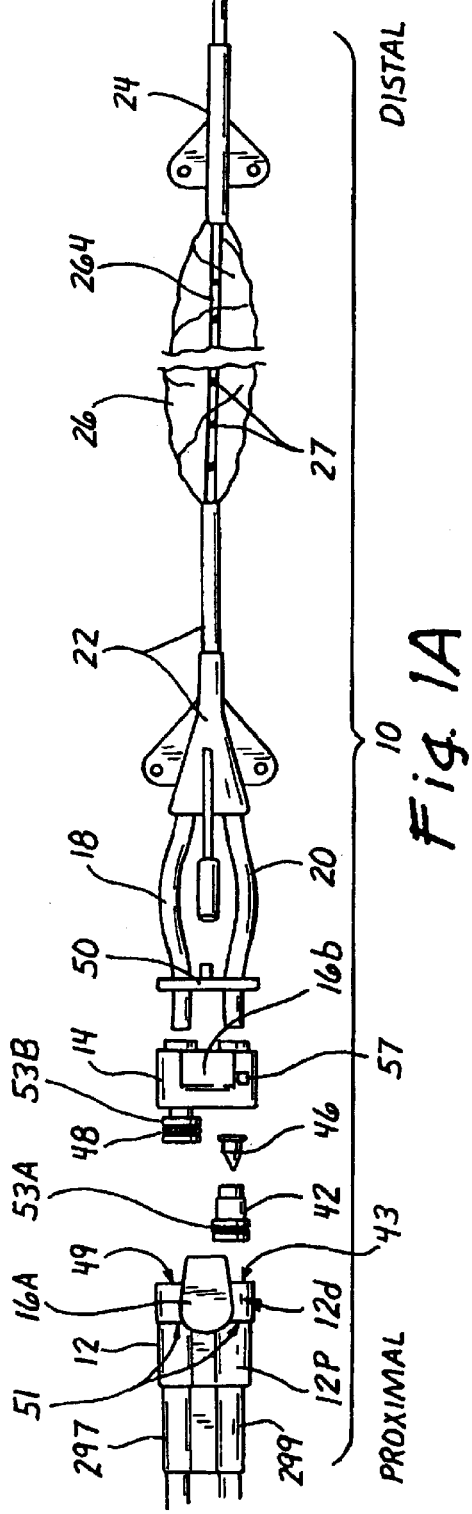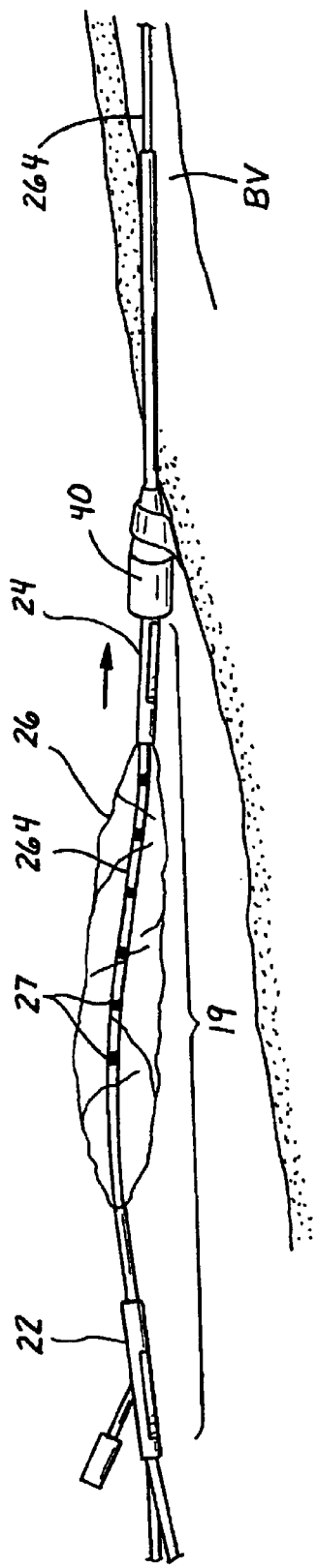

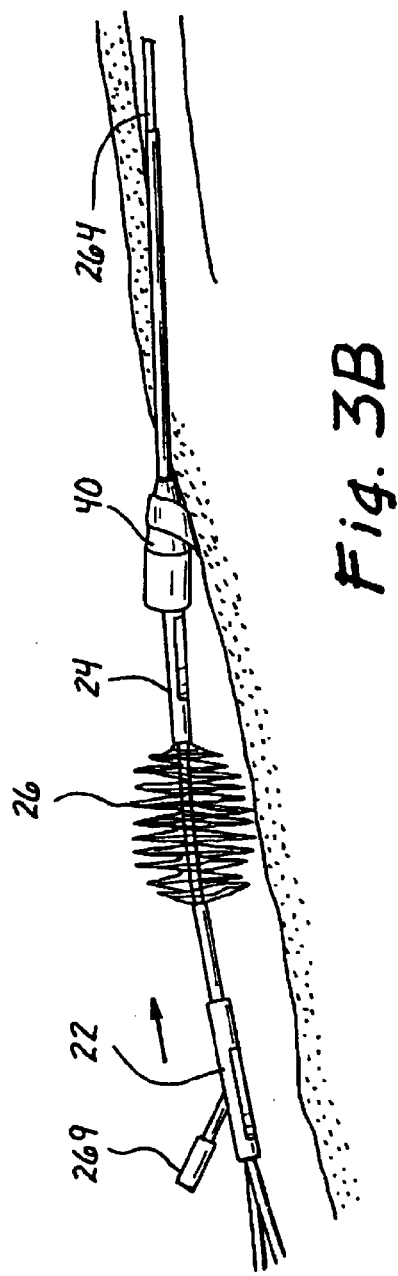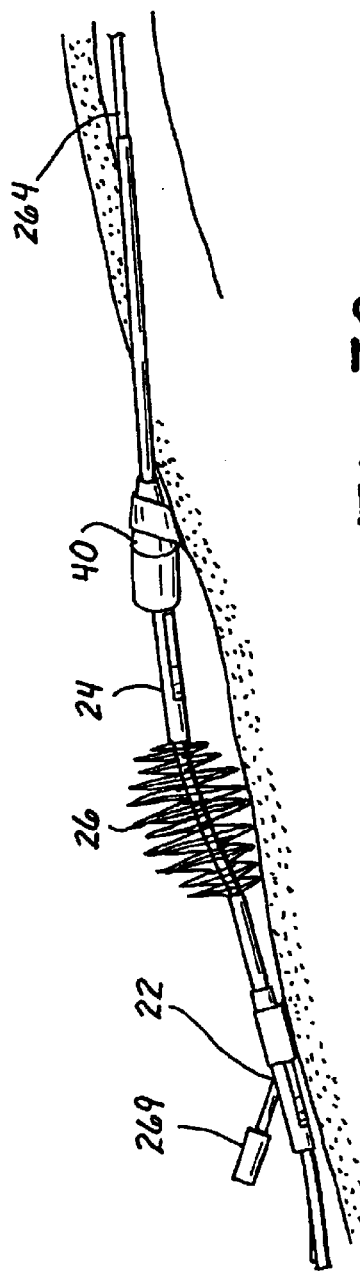

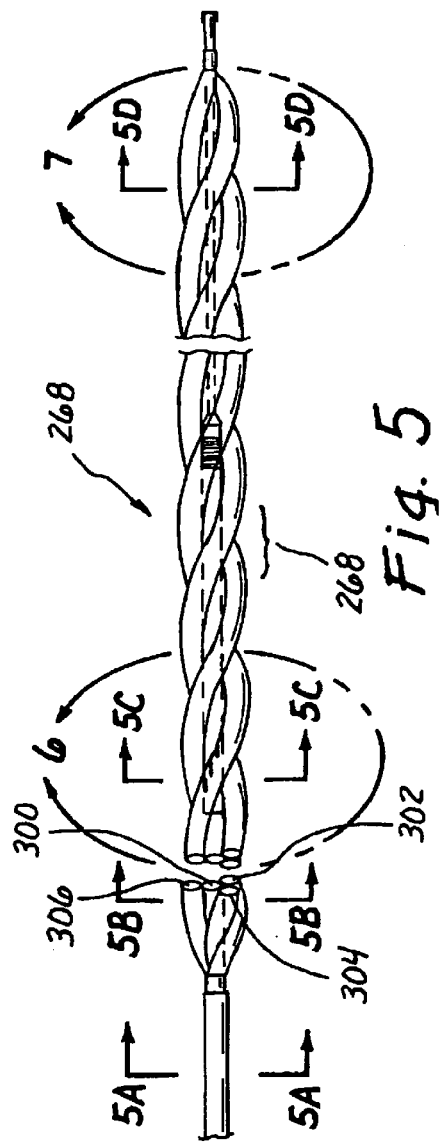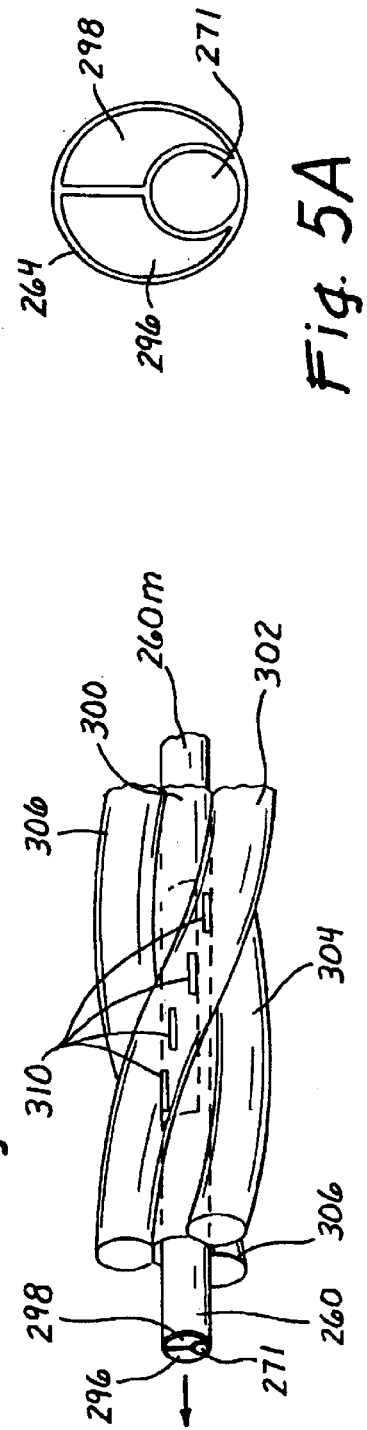

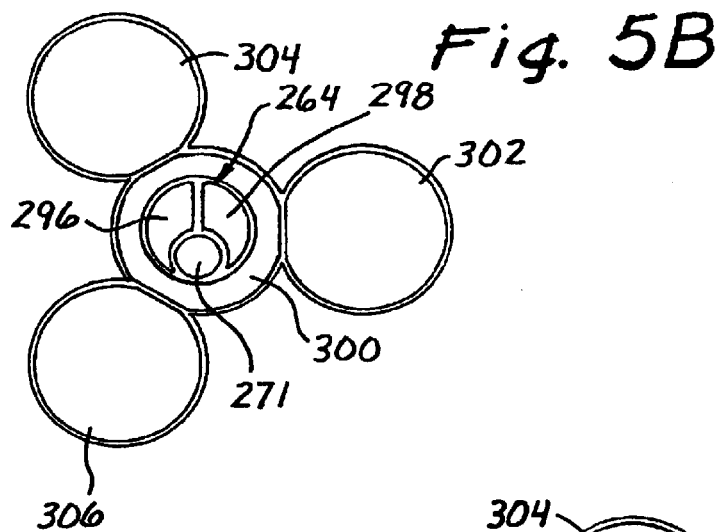
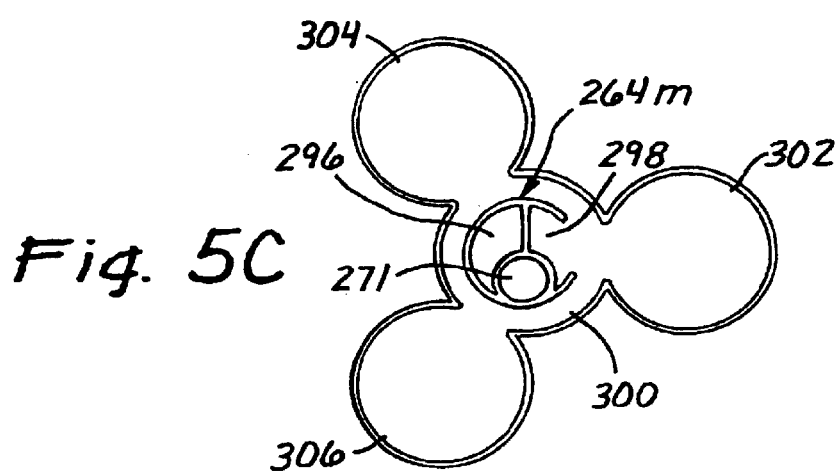
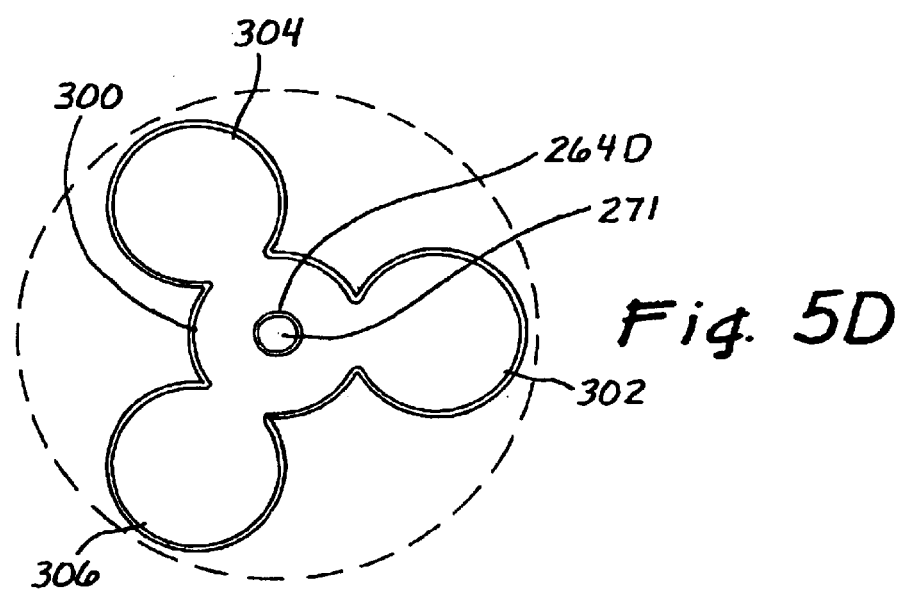

VALVED CONNECTOR ASSEMBLY AND STERILITY BARRIERS FOR HEAT EXCHANGE CATHETERS AND OTHER CLOSED LOOP CATHETERS

FIELD OF THE INVENTION

This invention relates generally to devices and methods for medical treatment and more particularly to catheters that are insertable into the bodies of human or veterinary patients and related methods.

BACKGROUND OF THE INVENTION

A. Closed Loop Catheters

The prior art has included numerous "closed loop" catheters having closed loop fluid flow circuits formed within the catheter. Examples of such closed loop catheters include various types of catheters that have a) a first lumen through which a fluid may flow into the catheter body and b) a second lumen through which fluid that has entered the catheter body through the first lumen may subsequently flow out of the catheter body. In some instances, a reservoir (e.g., chamber, vesicle, collector, space, etc.) may be formed on or within the catheter in fluid communication with the fist and second lumens such that fluid infused through the first lumen may collect within the reservoir and may subsequently flow out of the reservoir through the second lumen. Also, in some instances, the reservoir may have one or more flexible wall(s) and may be inflatable such that the reservoir expands when filled with fluid and collapses when fluid is evacuated from the reservoir. Examples of expandable reservoirs include various types of balloons including those which are elastic as well as those that are non-compliant and/or heat exchangers that may be formed on or in a catheter.

One specific type of closed loop catheter is an endovascular heat exchange catheter that may be inserted into a patient's blood vessel and used to heat or cool the blood flowing through that blood vessel and, hence, all or a portion of the patient's body. In these endovascular heat exchange catheters heated or cooled heat transfer fluid (e.g., saline solution) is circulated though a closed loop circuit. The closed loop circuit may include an expandable (e.g., inflatable) heat exchanger (e.g., a heat exchange balloon) that has a collapsed configuration when uninflated and an expanded configuration when inflated. Typically, endovascular heat exchange catheters that have expandable (e.g., inflatable) heat exchangers are inserted into the patient's vasculature through a small introducer or puncture tract while the heat exchanger is in its collapsed (e.g., uninflated) configuration. Thereafter, heat transfer fluid is circulated through the heat exchanger, causing it to assume its expanded (e.g., inflated) configuration. After the procedure has been completed, it is generally desirable to fully deflate the heat exchanger before attempting to reposition or remove heat exchange catheter from the patient's body to facilitate its passage through the relatively small diameter introducer/puncture site and to avoid possible damage to the patient's blood vessels. To accomplish such deflation of the heat exchanger, it may be desirable to apply negative pressure to the fluid lumen(s) of the catheter to ensure that the heat exchanger is fully deflated and in its fully collapsed configuration. Examples of such endovascular heat exchange catheters and related apparatus include those described in U.S. Pat. No. 5,486,208 (Ginsburg), PCT International Publication WO 00/10494 (Machold et al.), U.S. Pat. No. 6,264,679 (Keller et al.), PCT International Publication Nos. WO-00/10494 (Radiant Medical, Inc.) and WO 01/58397 (Radiant Medical, Inc.), all of which are expressly incorporated herein by reference.

There also exist various other types of "closed loop" catheters that have inflatable balloons or fluid-expandable members that must be fully deflated prior to movement or removal of the catheter from the body. Especially in cases where the balloon or fluid-expandable member is inflatable or expandable but not elastic, it may be desirable or even necessary to apply negative pressure to the catheter lumen(s) to fully deflate the balloon or fluid-expandable member to ensure its complete collapse before moving or removing the catheter from the body.

B. Sterility Barriers for Medical Catheters:

After any catheter has been inserted into a patient's vasculature, it is sometimes desirable to further advance or reposition the catheter. If a proximal portion of the catheter has become exposed to room air and possible microbial contamination, further advancement of that portion of the catheter into the patient's vasculature may risk introduction of microbial contamination into the patient's blood. Thus, the prior art has included various apparatus and methods for creating sterility barriers to prevent contamination of patients and/or medical devices, including those apparatus and methods described in U.S. Pat. No. 5,385,495 (Lynn), U.S. Pat. No. 5,775,328 (Lowe et al.), U.S. Pat. No. 4,491, 137 (Jingu), U.S. Pat. No. 4,646,772 (Silverstein et al.), U.S. Pat. No. 4,898,178 (Wedel), U.S. Pat. No. 5,341,810 (Dardel), U.S. Pat. No. 5,490,522 (Dardel), U.S. Pat. No. 5,498,230 (Adair) and PCT International Publication Nos. WO84/03034 (Drue et al.), WO97/49337 (Loxe et al.) And WO99/48424 (Lowe et al.).

Notwithstanding the prior art, there remains a need in the art for the development of new connectors for closed loop catheters to facilitate and verify complete evacuation of fluid from those catheter's closed loop fluid flow circuits and complete deflation of any expandable reservoirs (e.g., heat exchangers, balloons, etc.) formed in or on those closed loop catheters. Separately or in combination with such new connectors, there also remains a need in the art for the development of improved sterility barriers for maintaining sterility of the exteriorized portions of catheters that may be further advanced into the patient's body at a later time.

SUMMARY OF THE INVENTION

The present invention provides a closed loop catheter device that comprises (a) an elongate, flexible catheter body having a proximal end and a distal end, (b) a closed loop fluid flow circuit comprising a first lumen through which a fluid may flow into the catheter body and a second lumen through which fluid that has entered the catheter body through the first lumen may subsequently flow out of the catheter body, (c) a connector assembly on the proximal end of the catheter body, such connector being having an inflow lumen which is connectable to and disconnectable from an inflow fluid source and an outflow lumen which is connectable and disconnectable from an outflow fluid receiver into which fluid may flow out of the first lumen and, (d) a valving apparatus which closes at least one of the first and second lumens when the connector is disconnected from at least the inflow source such that fluid may then be evacuated from the closed loop circuit through the lumen that remains unclosed without concurrent entry of make-up air or other fluid into the closed loop circuit though the lumen that has been closed by the valving apparatus. Additionally, the closed loop circuit may incorporate a reservoir (e.g., a cavity, vessel, void, balloon, heat exchanger, compliant balloon, bag or expandable/inflatable region) between the first and second lumens. After the connector has been disconnected, negative pressure (e.g., suction) may be applied to the other lumen (e.g., the lumen that remains open to flow in the outward direction) to evacuate remaining fluid from the reservoir without re-entry of make-up air or make-up fluid into the reservoir through the closed lumen. In embodiments where the reservoir is expandable (e.g., a radially expandable balloon or heat exchanger), this procedure may be used to fully collapse (e.g., deflate) the reservoir (e.g., balloon or heat exchanger) prior to withdrawal or repositioning of the catheter. In some embodiments pressure indicating apparatus may be provided to indicate when the pressure within the closed loop circuit has fallen below a certain predetermined pressure and, accordingly, any expandable reservoir has been sufficiently deflated or collapsed to allow the catheter to be safely moved or withdrawn from the patient's body. Also, in some embodiments of the invention, the catheter may comprise a heat exchange catheter wherein the closed loop circuit and/or the reservoir comprise a heat exchanger and the fluid that is circulated through the closed loop circuit (and if present, the reservoir) comprises a heat transfer fluid such as saline solution, water or any other suitable fluid capable of being heated or cooled. Such heat exchange catheters may be used to warm or cool all or a portion of a patient's body. In some embodiments, the heat exchanger may comprise an expandable reservoir which expands and contracts in relation to the pressure of fluid within the heat exchanger. In such embodiments, the connector assembly of the present invention will facilitate rapid connection and disconnection of the catheter from its source of heat transfer fluid and will also provide a convenient means for attaching a deflation apparatus (e.g., a syringe) to extract remaining fluid from the closed loop flow circuit after the catheter has been disconnected from its source of heat transfer fluid.

Further in accordance with the present invention, there is provided a sterility barrier that is useable on virtually any type of catheter that is insertable into the body of a human or veterinary patient, such sterility barrier is configured to substantially surround an exteriorized portion of the catheter so as to substantially prevent contamination of the exteriorized portion of the catheter by microbes, dirt, chemical substances, etc. If it is subsequently desired to advance the catheter further into the patient's body, all of some of the exteriorized portion that has been substantially surrounded by the sterility barrier will be free of contamination and may be advanced into the patient's body without undo risk of infection or other untoward consequences that could result from introduction of a contaminated section of catheter into the patient's body. The sterility barrier may be generally tube-shaped and may be formed of thin, flexible plastic film. The sterility barrier may be transparent to allow visualization of the exteriorized portion of the catheter through the sterility barrier. Length markings may be formed on the exteriorized portion of the catheter to allow an operator to determine the length of catheter that resides within the patient's body at any given point in time. In some embodiments, a proximal hub member may be attached to a proximal end of the catheter and a distal hub member may be positioned distal to the proximal hub member with the body of the catheter being slidably advancable through the distal hub member. The sterility barrier may be affixed and sealed to the proximal and distal hub members and one or both of the proximal and distal hub members may be affixable to the patient's body (e.g, the hub member(s) may be taped to the patient's skin). In this manner, an exteriorized portion of catheter extending between the proximal and distal hub members will be substantially surrounded and shielded by the sterility barrier and some or all of such exteriorized portion may be subsequently advanced through the distal hub member and into the patient's body.

Further aspects and advantages of the present invention will be recognized and understood by those of skill in the art upon reading of the detailed description and examples of the invention set forth herebelow and in the accompanying drawings.

DETAILED DESCRIPTION OF THE DRAWINGS

FIG. 1A is an exploded view of the connector assembly and sterility barrier components of the catheter of FIG. 1.

FIGS. 3A–3C show in step-by-step fashion a method by which a sterility barrier assembly of the present invention may be used to microbial contamination of an exteriorized proximal portion of the catheter and to facilitate advancement or repositioning of the catheter subsequent to its initial insertion into a patient's body.

FIG. 5 is a side elevational view of the heat exchange catheter component of the automated endovascular heat exchange system of FIG. 2.

FIG. 5A is a cross-sectional view through line 5A—5A of FIG. 5.

FIG. 5B is a cross-sectional view through line 5B—5B of FIG. 5.

FIG. 5C is a cross-sectional view through line 5C—5C of FIG. 5.

FIG. 5D is a cross-sectional view through line 5D—5D of FIG. 5.

FIG. 6 is an enlarged, perspective view of the portion of the heat exchange catheter within circle 6 of FIG. 5.

DETAILED DESCRIPTION

Figure 1:
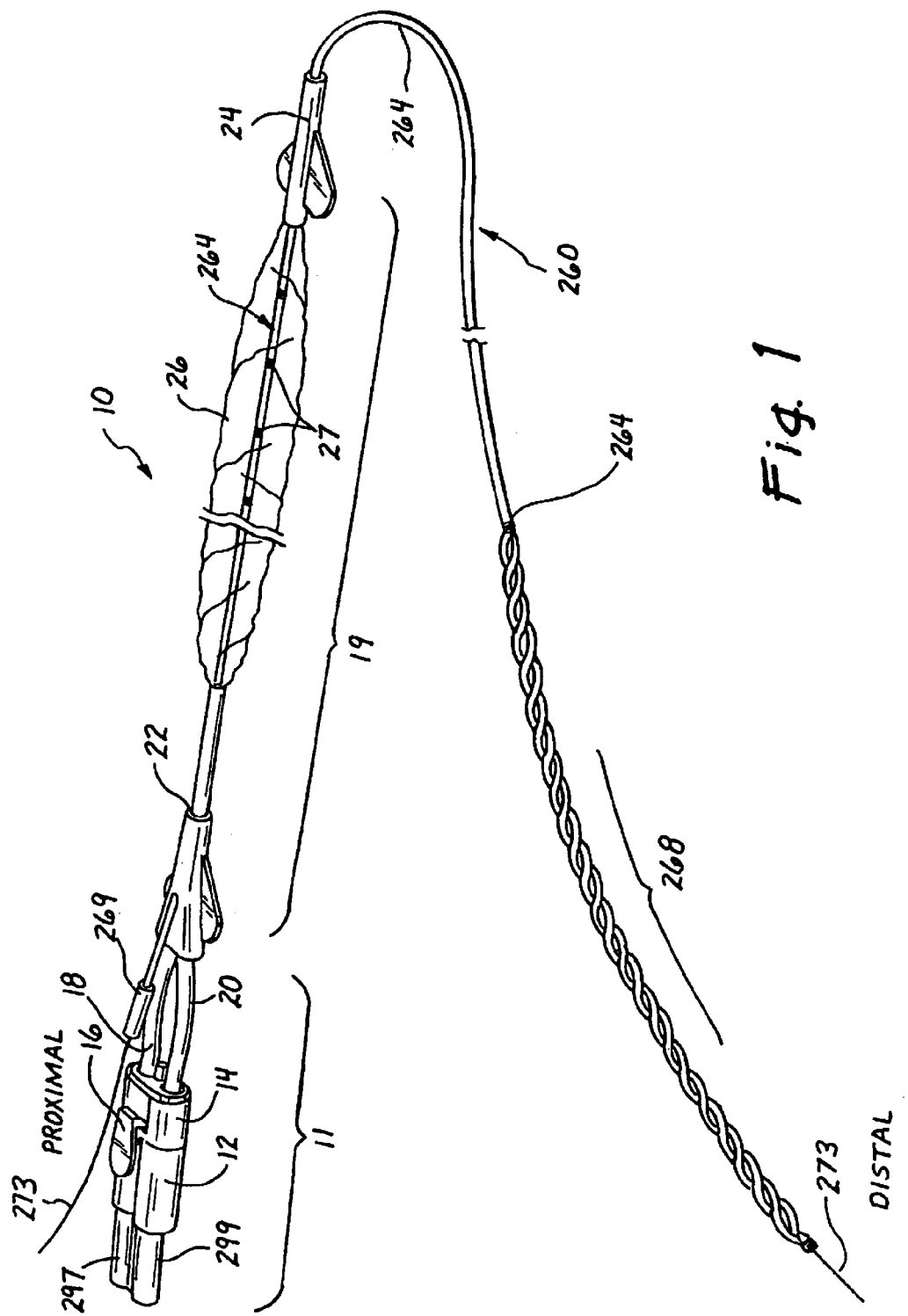
FIG. 1 is a perspective view of a closed catheter of the present invention having a connector assembly of the present invention on the proximal end of the catheter as well as a sterility barrier of the present invention for preventing microbial contamination of an exteriorized proximal portion of the catheter.

A. A Valved Connector & Sterility Barrier Assembly

Components and Construction of the Connector & Sterility Barrier Assembly

FIGS. 1–4c show an example of a valved connector and sterility barrier assembly 10 of this invention attached to one type of closed loop heat exchange catheter 260. The valved connector and sterility barrier assembly 10 comprises a connector portion 11 and a sterility barrier portion 19 which, although shown in combination in this example, may be provided and/or used separately as well.

The connector portion 11 includes a) a first connector body 12 that is attached to or formed on the ends of a fluid inflow source such as a fluid inflow tube 297 and a fluid outflow receptacle such as a fluid outflow tube 299, b) a second connector body 14 that is connectable to the first connector body 12, c) latches 16 for deterring inadvertent separation or disconnection of the first and second connector bodies 12 and 14 respectively, and d) a catheter inflow feed tube 18 and catheter outflow receiving tube 20.

Figure 7:
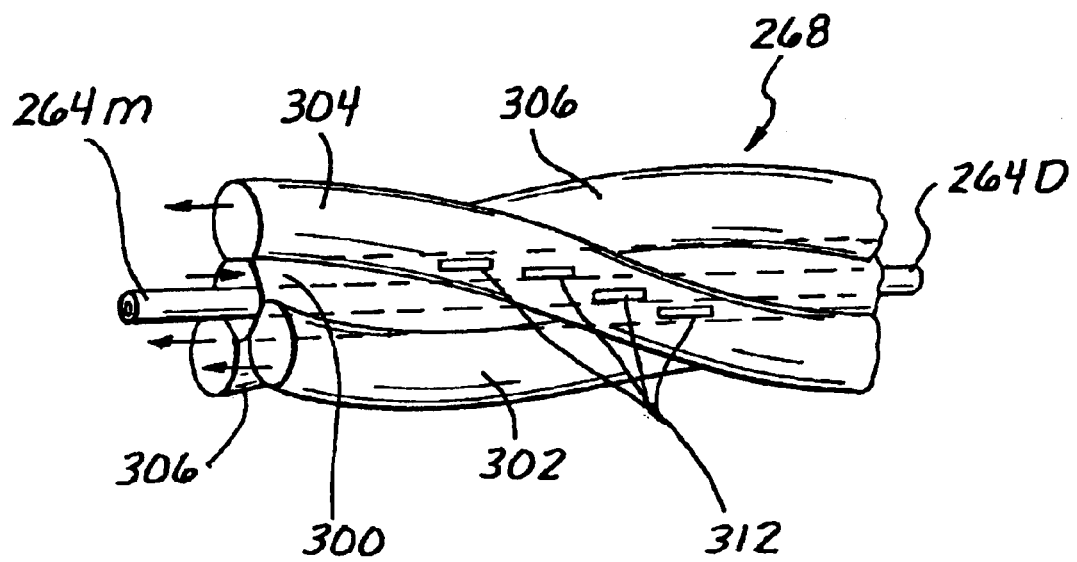
FIG. 7 is an enlarged, perspective view of the portion of the heat exchange catheter within circle 7 of FIG. 5.

The sterility barrier portion 19 includes a) a proximal hub member 22, b) a distal hub member 24 and c) a generally tubular sterility barrier sleeve 26 that is affixed to and extends between the proximal hub member 22 and the distal hub member 24. In this example, the connector and sterility barrier assembly 10 is shown in conjunction with a heat exchange catheter device 260. The particular heat exchange catheter device 260 of this example generally comprises an elongate, flexible catheter body 264 and an expandable/collapsible heat exchanger 268 positioned on the distal end of the catheter body 264. Details of this particular heat exchange catheter device 260 are shown in FIGS. 5–7 and are described in further detail herebelow.

The connector portion 11 of the assembly 10 functions to permit the catheter 260 to be rapidly connected and disconnected to an inflow fluid source (such as inflow tube 297) and an outflow fluid receptacle (such as an outflow tube 299). Thus, heated or cooled heat transfer fluid may be circulated through the catheter body 264 and heat exchanger 268. This connector portion 11 of the assembly 10 also facilitates complete deflation and contraction or collapse of the heat exchanger 268 following completion of a patient treatment procedure, thereby ensuring that the heat exchanger is fully collapsed (i.e., fully reduced in diameter) before the catheter 260 is moved or withdrawn from the patient's body.

The sterility barrier portion 19 of the assembly 10 functions to substantially encapsulate and deter microbial or other contamination of that portion of the catheter body 264 that is, at that point in time, positioned between the proximal hub member 22 and the distal hub member 24.

Figure 2:
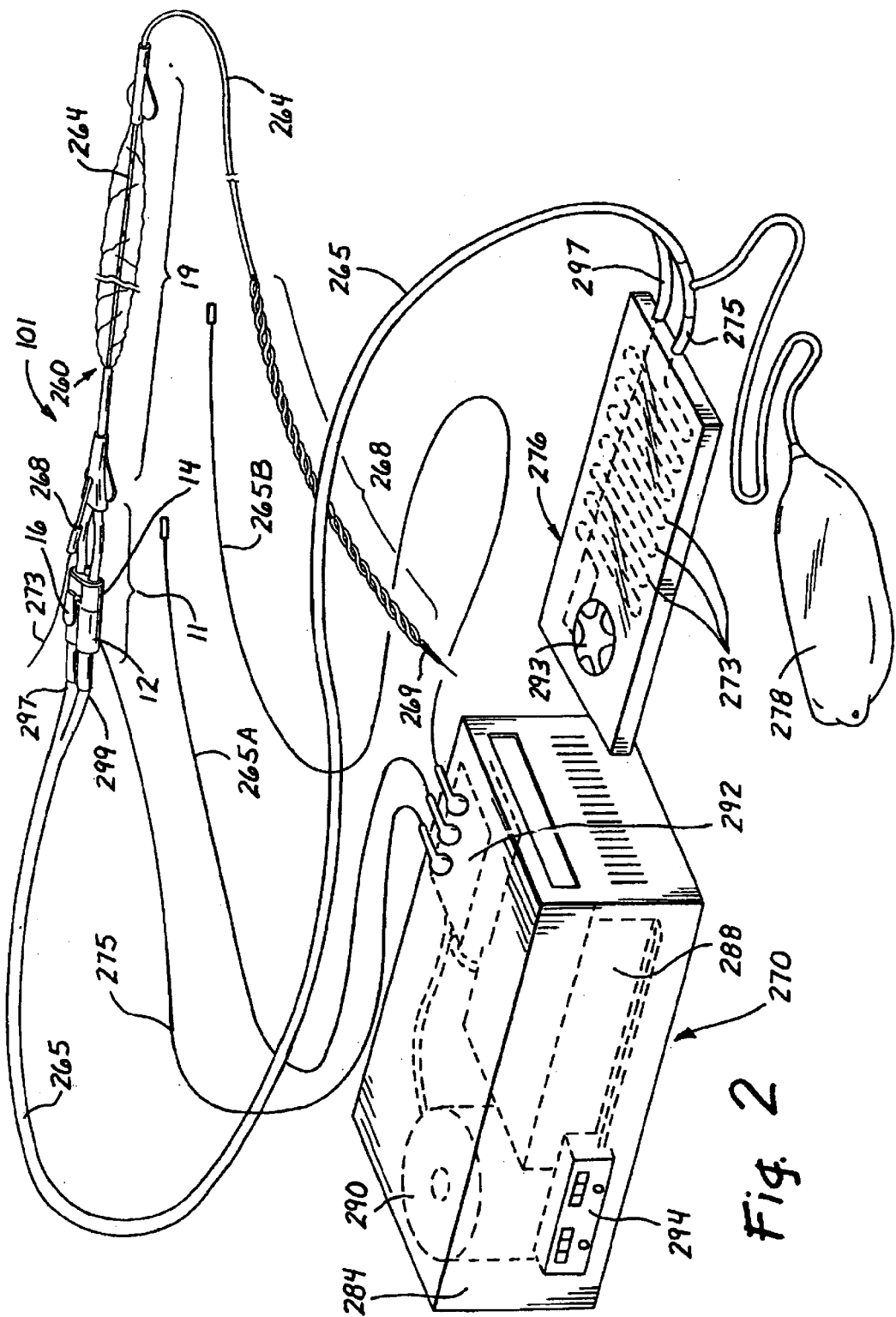
FIG. 2 is a perspective view of one type of automated endovascular heat exchange system incorporating a heat exchange catheter that includes a connector assembly of the present invention on the proximal end of the catheter as well as a sterility barrier of the present invention for preventing microbial contamination of an exteriorized proximal portion of the catheter.
Figure 4A:
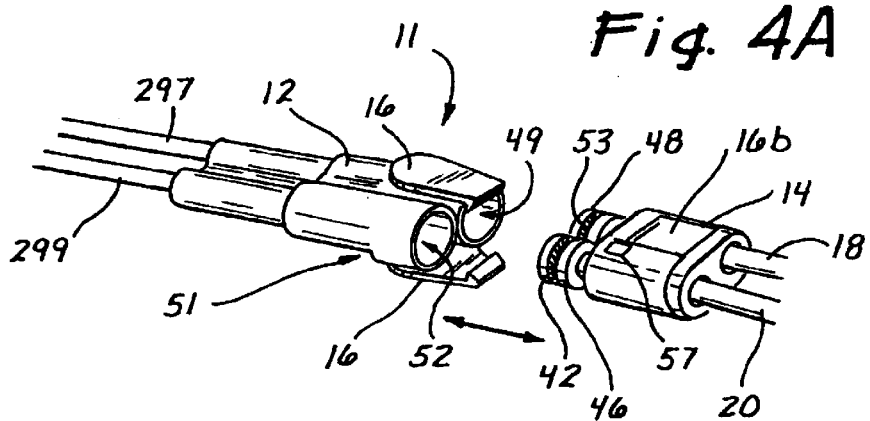
FIGS. 4A–4C show in step-by-step fashion a method by which a connector assembly of the present invention may be used to accomplish disconnection of a closed loop catheter from a fluid source and subsequent evacuation of residual fluid from the catheter's closed loop fluid flow circuit.

Certain details of the construction of the connector & sterility barrier assembly 10 may be appreciated from the exploded view of FIG. 1A and the perspective showing of FIG. 4a. As shown in this example, the first connector body 12 comprises a rigid body which has inflow and outflow lumens or bores extending longitudinally therethrough. The distal portion 12d of the first connector body 12 is enlarged and the diameters of the inflow and outflow bores are greater in the distal portion 12d than in the proximal portion 12p of the first connector body 12. Annular shoulders or stepdowns 51 are thus formed in the walls of the inflow and outflow bores of the first connector body 12, thereby defining enlarged distal bores 43, 49 of the bores which are open through the distal end of the fist connector body 12. This first connector body 12 may be attached to or formed on the ends of fluid inflow 297 and fluid outflow 299 tubes such that the fluid inflow will pass through one bore of the fist connector body 12 and the fluid outflow will pass through the other bore of the first connector body 12. As will be appreciated from FIG. 2 (and the description of FIG. 2 provided herebelow) the inflow tube 297 and outflow tube 299 may be in the form of separate tubes or may comprise separate lumens within a multi-lumen flow conduit 265. First latch components comprising pawls 16a are attached to or formed on the first connector body 12, as shown.

The second connector body 14 also comprises a rigid body that has inflow and outflow lumens or bores extending longitudinally therethrough. Second latch components comprising pawl-receiving notches or depressions 16b are formed on the top and bottom surfaces of the second connector body 14. Male tubular projections 42, 48 extend from the proximal end of the second connector body 14. One male tubular projection 48 is continuous with the inflow bore of the second connector body 14 and another male tubular projection 42 is continuous with the outflow bore of the second connector body 14. O rings 53a, 53b are seated within grooves formed about the tubular projections 42, 48. A one way valve 46, such as a duckbill valve or other suitable type of check valve known in the art, is mounted within the outflow bore of the second connector body 14. In some embodiments, the one way valve 46 may operate continuously to block flow in the inflow direction through the outflow bore irrespective of whether or not the first connector body 12 is connected to the second connector body 14. However, in other embodiments, the one way valve may become activated such that it blocks flow in at least the inflow direction through the outflow bore of the second connector body 14 only when the first connector body 12 is separated from the second connector body 14. For example, a projection (not shown) may extend in the distal direction from the outflow side of the first connector body 12 such that it becomes inserted into the outflow bore of the second connector body 14 when the first and second connector bodies 12 and 14 are placed in their joined or connected positions (FIG. 1) and one or more hinged or flexible valve leaflets or moveable bulkheads may be disposed within the outflow bore of the second connector body 14 such that such projection will force the hinged or flexible valve leaflets or moveable bulkheads to an open position when the first and second connector bodies 12,14 are placed in their connected or joined positions (thereby allowing flow in both directions through the outflow bore of the second connector body 14) and the hinged or flexible valve leaflets will spring closed or otherwise become closed when the first and second connector bodies 12,14 become separated from one another (thereby preventing flow in at least the inflow direction through the outflow bore of the second connector body).

Inflow feed tube 18 and outflow feed tube 20 extend through a rigid guide member 50 and are attached to the distal end of the second connector body 14 to connect its inflow and outflow bores to the catheter body 264.

When the first connector body 12 and second connector body 14 are connected to one another, the male tubular projections 42, 48 are received within the enlarged distal portions 43, 49 of the bores of the first connector body 12 until the ends of the male projections 42, 48 abut against the annular shoulders 51 formed in the walls of the first connector body's bores. The pawls 16a of the first connector body 12 are inwardly biased such that they snap fit into the corresponding notches 16b in the second connector body 14, thereby holding the first connector body 12 and second connector body 14 in connection with one another. When it is desired to disconnect the connector bodies 12, 14, the proximal ends of the pawls 16a are depressed causing the distal ends of the pawls 16a to lift out of notches 16b and the proximal connecter body 12 is pulled away and separated from the distal connector body 14.

After the connector bodies 12, 14 have been separated, a syringe SYR or other source of negative pressure may be attached to tubular projection 48 and used draw residual fluid out of the catheter body 264 and heat exchanger 268, thereby causing heat exchanger 268 to assume a collapsed configuration in which the diameter of the heat exchanger 268 is only slightly larger than the diameter of the catheter body 264 adjacent to the heat exchanger 268. The one way valve 46 prevents air from entering the catheter body 264 or heat exchanger 268 during this deflation process, thus ensuring that the heat exchnager may be fully collapsed.

An optional pressure indicator 57 may provide an indication of the pressure within the catheter's closed loop circuit or at least an indication of when the pressure within the closed loop circuit is sufficiently low or negative to ensure that the heat exchanger has been collapsed to a diameter that would allow the catheter 260 to be moved or withdrawn from the body without hanging up on the introducer through which the catheter 260 is inserted and without causing trauma to the patient's vasculature. This optional pressure indicating apparatus may comprise any suitable type of pressure indication, including a simple dome made of plastic that inverts to form a dimple when the pressure within the closed loop circuit is sufficiently negative to ensure adequate deflation of the heat exchanger (or any other expandable item on the catheter, such as a balloon). In some embodiments, there may also be an optional disabling apparatus that renders the catheter non-reusable after the fluid has been evacuated from the closed loop flow circuit. This will deter unauthorized reuse of a previously used catheter 260. In this regard, in embodiments having a pressure indicator that inverts or dimples inward in response to negative pressure within the closed loop circuit, such apparatus my comprise or include a lumen blocker or bulkhead that would prevent subsequent flow of fluid through the closed loop circuit one the heat exchanger 268 (or balloon or other expandable aspect of the catheter 260) has been deflated by application of negative pressure.

The sterility barrier assembly can also be appreciated from the showing of FIG. 1a. As shown, the proximal hub member 22 and distal hub member 24 may be provided with laterally extending wings or otherwise configured so as to facilitate taping of the hub members 22, 24 to the patient's skin. The sterility barrier sleeve 26 may comprise a tube formed of clear, flexible plastic film having a thickness in the range of about 0.5 mills to about 10 mills, and preferably approximately 2 mills. Distance interval markings 27 may be formed on a proximal portion of the catheter body 264 to provide visual indicia of the length of catheter body 264 that has been advanced through the distal hub member 24 relative to the length of catheter body 264 that remains within the sterility barrier 264.

Method of Use of the Connector & Sterility Barrier Assembly

A method for using the connector & sterility barrier assembly 10 is shown in FIGS. 3a–3c and 4a–4c. As shown, the catheter 260 is typically inserted into the patient's vasculature using a Seldinger technique wherein a tubular introducer sheath 40 is inserted into a blood vessel BV and the catheter body 264 is then advanced through the introducer 40 and into the blood vessel BV. The catheter body 264 may then be advanced through the vasculature until the heat exchanger 268 is at the desired position. The tubular distal portion of the distal hub member 24 may be received within the hub of the introducer 40, as shown in FIG. 3a. In some embodiments, the hub of the introducer 40 may be custom made to mate with the distal portion of the distal hub member 24 so that the hub member 24 may snap fit, bayonet lock or otherwise form a contamination proof seal and/or locking connection with the hub of the introducer 40. The catheter body 264 remains slidably advanceable and retractable through the distal hub member 24 and introducer 40. In some cases the distal hub member 24 may not actually inserted into the hub of the introducer 40, but may remain a spaced distance behind the hub of the introducer 40. In ether case, the distal aspect of the distal hub member 24, the hub of the introducer 40 and any portion of the catheter body 264 exposed therebetween may optionally be covered with a sterile dressing as is common in the art, thereby further deterring microbial or other contamination of the exteriorized portion of the catheter body 264. The remainder of the exteriorized portion of the catheter body resides between the hub members 22, 24 and is protected from contamination by the sterility barrier sleeve 26. As shown in FIGS. 3b–3c, when it is desired to further advance the catheter body 264 into the patient, the operator may grasp the catheter body 264 through the sterility barrier 26 and may push the catheter body 264 in the distal direction through the distal hub member 24, through the introducer sheath 40 and onto the patient's vasculature, thereby causing the flexible sterility barrier 26 to pucker and causing the proximal hub member 22 and distal hub member 24 to be drawn closer to one another. Both hub members may then be re-taped to the patients skin, thereby holding the catheter body 264 in the presently advanced position. Similarly, if it is later desired to pull the catheter body back to a different position, the operator may repeat the above-described process, drawing the catheter in the proximal direction and causing the hub members 22, 24 to become further apart from one another.

Figure 4B:
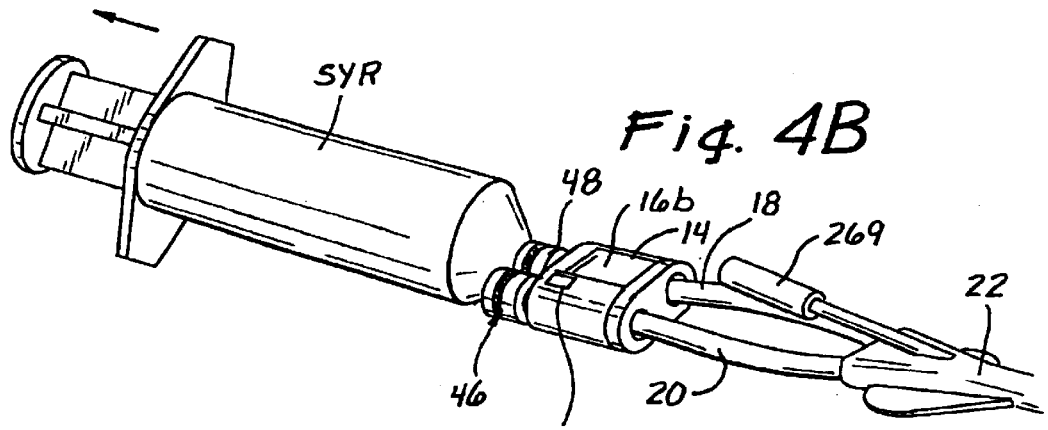
Figure 4C:
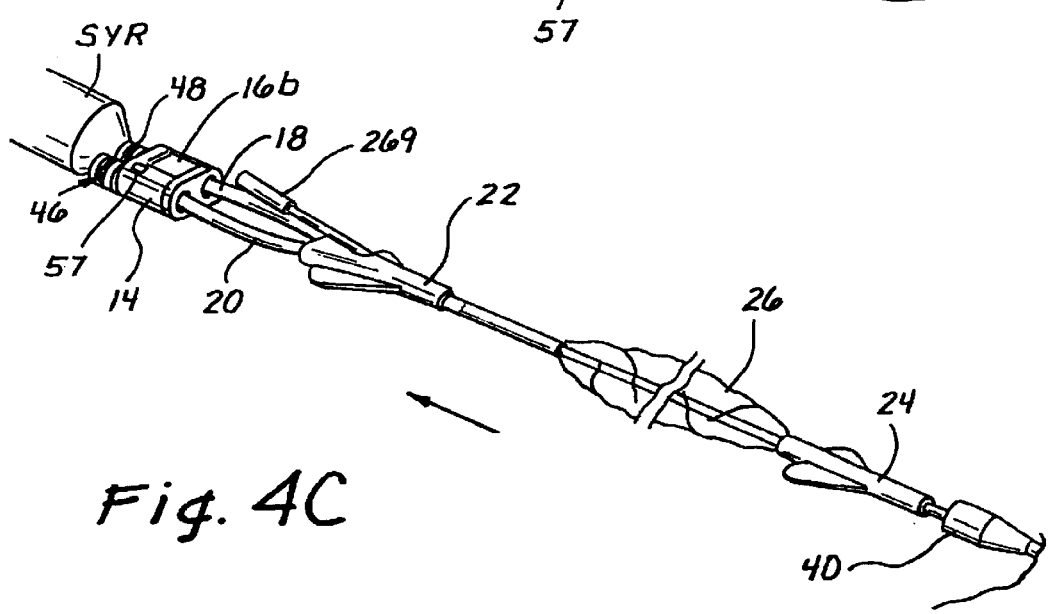

With particular reference to FIGS. 4a–4c, the connector bodies 14, 12 are connected to one another by inserting the tubular projections 42, 48 into bores 43, 49 of the fist connector body 12 and allowing pawls 16a to snap into detents 16b, thereby locking the first connector body 12 and second connector body 14 together. When it is subsequently desired to disconnect the catheter, the proximal ends of the pawls 16a are depressed causing their opposite ends to disengage from detents 16b and the first connector body 12 and second connector body 14 are pulled apart as shown in FIG. 4a. After the connector bodies 12, 14 have been separated, a syringe SYR or other source of negative pressure is attached to tubular projection 48 and used to draw residual fluid out of the catheter body 264 and heat exchanger 268, thereby causing heat exchanger 268 to assume a collapsed configuration in which the diameter of the heat exchanger 268 is only slightly larger than the diameter of the catheter body 264 adjacent to the heat exchanger 268. The one way valve 46, as shown in FIG. 1a, prevents air from entering the catheter's closed loop flow circuit though the other tubular projection 42 as negative pressure is applied by the syringe SYR. In situations where the assembly 10 includes the optional pressure indicator 57, the operator may continue to withdraw the plunger of the syringe until the optional pressure indication indicates that the negative pressure within the catheter's closed loop flow circuit is sufficient to ensure that the fluid has been adequately removed from the closed loop circuit and/or any expandable portion of the catheter (e.g., balloon, heat exchanger, etc.) has been sufficiently deflated to allow safe movement and withdrawal of the catheter 260 from the patient's body. In embodiments where the assembly 10 further comprises an optional disabling apparatus as described above, this process of evacuating the catheter's closed loop circuit may also cause the optional disabling apparatus to permanently block or impede flow through the catheter's closed loop flow circuit so that the catheter can not easily be reused.

B. An Endovascular Temperature Control System Incorporating an Introducer Sheath/Temperature Probe Assembly Various types of heat exchange catheters and related apparatus may be used in conjunction with the valved connector and sterility barrier assembly 10 to alter and/or control the temperature of all or a portion of the body of a human or veterinary patient. Examples of such heat exchange catheters and related apparatus are described in U.S. Pat. Nos. 6,149,676 and 6,149,676 and co-pending U.S. patent application Ser. Nos. 09/138,830, 09/563,946 and 09/707,257, the entireties of which are expressly incorporated herein by reference. FIG. 2 shows one particular endovascular heat exchange system 101 which comprises an valved connector and sterility barrier assembly 10 of the present invention in combination with a re-usable heater/cooler/control unit 270 and a plurality of disposable components including a heat exchange catheter 260, a heat exchange cassette 276, a saline bag or fluid reservoir 278 and a plurality of fluid flow conduits including a two-way conduit 265 one end of which attaches to the heat exchange cassette 276 and the other end of which terminates in the first connector body 12 of the connector & sterility barrier assembly 10. Optionally, the system 101 may further include one or more additional body temperature probes or sensors 265a, 265b.

The re-usable heater/cooler/control unit 270 includes an outer housing 284 having a cassette insertion slot 285 into which the heat exchange cassette 276 may be inserted. A heater/cooler 288 such as a thermoelectric plate, a pump driver 290, and a microprocessor controller 292 are positioned within the housing 284. In addition, a manual input unit 294 enables an operator to enter desirable operating parameters into the microprocessor controller 292, for example a pre-selected target body temperature. Each of the electronic devices provided within the control unit 270 communicate through suitable wiring or other connections. Additionally, wire(s) other connection(s) (e.g., a wireless connection or fiber optic connection) connect the body temperature sensor(s) 265a, 265b as well as a heat transfer fluid temperature sensor and/or flow sensor 275 located on the catheter 260, to the microprocessor controller 292. Thus, signal(s) indicating the patient's body temperature as well as signal(s) indicating the temperature and or flow rate of the heat exchange fluid entering and/or exiting the heat exchange catheter 260 are received by the microprocessor controller 292.

In this example, the microprocessor/controller 292 may receive indications of a) patient body temperature as sensed by body temperature sensor(s) 267a, 267b, b) temperature and/or flow rate of heat exchange fluid flowing through the closed loop flow circuit of the heat exchange catheter 260 as sensed by sensor 261 and c) other parameters or targets (e.g., maximum rate of cooling or warming) input by the operator through the manual input unit 294. As those of skill in the art will appreciate, other sensed or operator-input parameters or variables may also be received by the microprocessor controller 292.

The heat exchange catheter 260 may comprise any suitable type of catheter designed to exchange heat with the patients blood, including those heat exchange catheters described in U.S. Pat, No. 5,486,208 (Ginsburg), PCT International Publication WO OO/10494 (Machold et al.), U.S. Pat. No. 6,264,679 (Keller et al.), PCT International Publication Nos. WO-00/10494 (Radiant Medical, Inc.) and WO 01/58397 (Radiant Medical, Inc.), the entireties of which are expressly incorporated herein by reference. One presently preferred heat exchange catheter 260 for use with this system 101 is shown in FIGS. 2 and 5–7. This particular heat exchange catheter 260 comprises a flexible catheter body or catheter shaft 264 and a heat exchange balloon 268. A working lumen 271 extends from a proximal port 268 through the catheter shaft 264 and terminates in an opening in the distal end of the catheter shaft 264. This working lumen 271 may be used for passage of a guidewire 273 and/or other optional apparatus, sensors, probes or other devices (e.g, temperature monitoring probes, pH measuring probes, etc.) and/or for injection/infusion of substances (e.g., radiographic contrast medium, drugs, fluids, etc.). Additionally an inflow lumen 296 extends from the inflow port 297, through the inflow bore of the connector assembly 11, through the catheter shaft 264 and into the interior of the heat exchange balloon 268. A outflow lumen 298 extends from the interior of the heat exchange balloon 268, through the catheter shaft 264, through the outflow bore of the connector assembly 11 and to the outflow port 299.

Two way flow conduit 265 has inflow and outflow lumens (not shown) extending therethrough. Bifurcations are formed on both ends of the two way flow conduit 265, as shown in FIG. 2. In this manner, the inflow lumen side of the two way flow conduit 265 is connected between the outflow port 297 of the cassette 276 and the inflow bore of the connector assembly 11 and the outflow lumen side of the two way flow conduit 265 is connected between the outflow bore of the connector assembly 11 and the inflow port 275 of the cassette 276.

As shown in FIGS. 5–7, the preferred heat exchange balloon 268 comprises a multi-lobed structure. The exact number of balloon lobes may vary depending on the particular application for which the heat exchange catheter 260 is being used and/or the size of the blood vessel in which the heat exchange balloon 268 is to be positioned. Preferably the heat exchange balloon 268, when fully inflated, will have a maximum diameter that is at least slightly smaller than the internal diameter of the blood vessel lumen in which it is positioned, thereby allowing blood to flow freely around the inflated heat exchange balloon 268. In this example, the heat exchange balloon 268 comprises four (4) tubular lobes, a central lobe 300 and three (3) outer lobes 302, 304, 306 that are helically wound about the central lobe 300. As can be seen in FIGS. 5 and 6, the catheter shaft 264 extends into and is joined with the central lobe 300 of the balloon. As may be appreciated particularly from the showings of FIGS. 5A, 5B and 5C and 6, the outflow lumen 298 of the catheter shaft 264 is connected via outflow slots 310 to the interior of the heat exchange balloon 268 such that heat transfer fluid may flow from the interior of the heat exchange balloon 268, through outflow slots 310, through outflow lumen 298, though outflow port 299, through the outflow lumen of two way conduit 265 and into the interior of the heat exchange cassette 276 through its inflow port 297. As shown in FIGS. 5–7, a medial catheter shaft 264M which includes a continuation of the inflow lumen 296 and working lumen 271 extends distally through the central lobe 300 of the heat exchange balloon 268 beyond the outflow slots 310 to the distal portion of the balloon where the inflow lumen 296 is connected to the interior of the heat exchange balloon 268 through inflow slots 312. Thus, a pump 293 mounted within the cassette 276 may pump heat transfer fluid from the open inner chamber of the cassette 276, through a convoluted or serpentine flow path defined by a convoluted or serpentine bulkhead or flow director 273 positioned within the cassette 276, through the outflow port 275 of the cassette 276, through the inflow lumen of two way conduit 265, through the inflow port 297, through the inflow lumen 296 of catheter shaft 264 and medial catheter shaft 264M, through inflow slots 312 and into the interior of the heat exchange balloon 268. In this manner heat transfer fluid that has become heated or cooled within the cassette 276 will enter the distal portion of the heat exchange balloon 268 and circulate generally in the proximal direction, exiting from the proximal portion of the heat exchange balloon 268.

C. Automated Control of Patient Temperature Using the Endovascular Temperature Control System with the Valved Connector & Sterility Barrier Assembly In typical use, the heat exchange catheter 260 with its heat exchange balloon 268 in a non-inflated, collapsed state, is percutaneously inserted through an introducer 40 as described hereabove and shown in FIGS. 3*a*–3*c*. The heat exchange catheter 260 is then advanced to a position wherein the heat exchange balloon 268 is positioned within the patient's inferior vena cava (IVC) or other desired location. In some cases, it may be desirable to initially insert the catheter to a position where the catheter's heat exchanger 268 is thought to be properly positioned and to subsequently take an x-ray to verify the position of the heat exchanger 268 and, at that time, the distal hub member 24 of the sterility barrier assembly 19 is sealed to the hub of the introducer 40 and/or covered with a sterile dressing and the sterility barrier 25 protects the portion of the catheter body 260 that remains exteriorized from contamination. The proximal hub member 22 of the sterility barrier assembly 19 may be taped to the patients body to hold the catheter body 264 in substantially fixed longitudinal position such that it will not inadvertently advance or retract. If it is determined from the x-ray that the heat exchanger 268 is not optimally positioned, it may be desirable to free up the proximal hub member 22 and move or reposition the catheter 260. In so doing, the operator may grasp the exteriorized portion of the catheter body 264 through the sterility barrier 26 and retract or advance the catheter body as described above and shown in FIGS. 3*b*–3*c*.

One or more body temperature sensor(s) 267*a*, 267*b* as shown in FIG. 2 is/are inserted into or positioned on the patient's body to provide feedback of the core body temperature or temperature of a particular body part. A bag or vessel 278 containing a suitable heat transfer fluid, such as sterile 0.9% NaCl solution, is attached to the proximal inflow furcation of the two way flow conduit 265 and the first connector body 12 attached to the distal end of the two way flow conduit 265 is connected with the second connector body 14 such that the distal ends of the pawls 16*a* of latch 16 snap into the detents 16*b* (see FIG. 4*a*) on the second connector body 14, thereby locking the connector bodies 12, 14 together, as shown in FIG. 2. The heat transfer fluid is then transferred from the bag or vessel 278 to fill the cassette 276, both lumens of the two way flow conduit 265, the connector assembly 11, connector assembly feed and return tube extensions 18 and 20, the inflow 296 and outflow 298 lumens of the proximal and medial portions of the heat exchange catheter shaft 264, 264M and the lobes 300, 302, 304, 306 of the heat exchange balloon 268. This causes the heat exchange balloon to assume its inflated configuration as shown in FIGS. 5–7. Any large air bubbles are purged such that the heat transfer fluid within the system 101 is substantially free of large air bubbles.

The cassette 276 is inserted into the cassette receiving slot 285 such that the cassette is positioned adjacent to the heater/cooler 288 and the pump driver 290 engages the pump 293. The operator inputs the target body temperature into the input apparatus 294. The system 101 is then energized and the controller receives the temperature signals from the temperature sensors 267A, 267B within the probe 32 and compares the sensed temperatures. If the difference between the temperatures sensed by the first sensor 40A and the second sensor 40 B is greater than the preset allowable difference (e.g., 1 degree difference) the controller will issue a warning signal to the operator and/or will automatically shut down or prevent start up of the pump driver 290, thereby stopping or preventing any heat transfer fluid from being circulated through the heat exchange balloon 268. If, on the other hand, the difference between the temperatures sensed by the first sensor 40A and the second sensor 40 B is no more than a preset allowable difference (e.g., 1 degree) the controller will average the two sensed temperatures and that average will be taken as the current measured body temperature to use as the "driver" temperature. Alternatively, the controller may compare the two signals, and if they are within the predetermined range (e. g. 1 degree C. or 10% or some other appropriate criteria) the controller may ignore one and use the temperature signal from the other as the temperature signal to drive the controller. As yet another alternative, the controller may compare the two signals and select one based on some other criteria, for example if the controller is cooling the patient's body, the controller may select the cooler of the two temperatures as the "driver" temperature to use, and thus avoid overcooling the patient, or if the controller is warming, it may select the warmer of the two as the "driver" temperature signal. If three signals are compared, the controller could also use the median temperature signal as the "driver" signal. These and other similar methods of comparing and using multiple temperature signals are all anticipated by this invention.

The controller 292 then compares this current body temperature to the target body temperature that had been entered by the operator and, if the current measured body temperature is different from the target temperature, the controller will cause the heater/cooler to either heat or cool the heat transfer fluid within the cassette 276 and/or will adjust the rate at which the driver 290 drives the pump 293 such that the temperature of the heat transfer fluid being circulated through the heat exchange balloon 268 and/or the rate at which the heat transfer fluid is circulated through the heat exchange balloon 268 will cause warming or cooling of the patient's blood until the current measured body temperature reaches the target temperature. The controller 292 may be specifically programed to minimize or prevent overshoot of the target temperature as described in U.S. Pat. No. 5,837,003 (Ginsburg) and U.S. Pat. No. 6,149,673 (Ginsburg) and PCT International Patent Publication No. WO-00/10494 (Radiant Medical, Inc.), the entire disclosures of which are expressly incorporated herein by reference. After the target body temperature has been attained, the controller will continuously or periodically redetermine the current measured body temperature and will cause corresponding adjustments in the heater/cooler and or pump driver 290 to maintain the patient's body temperature at or near the target temperature (e.g., target temperature + or −0.5 degrees C.).

After the procedure is completed, heater/cooler 288 and pump 290 are de-energized. The pawls 16*a* of latch 16 are depressed and the first connector body 12 is separated from the second connector body 14 in the manner depicted in FIG. 4*a*. Thereafter, as described in detail hereabove and shown in FIGS. 4*b*–4*c*, a syringe SYR is attached to the inflow tubular projection 48 and is used to remove heat exchange fluid from the catheter 260 and to ensure that the heat exchanger 268 is fully collapsed before the catheter 260 is withdrawn through the lumen of the introducer sheath 40 and out of the patient's body. Thereafter, the introducer sheath 40 may be removed.

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process, process step or steps, while remaining within the scope of the present invention. Accordingly, the scope of the invention should therefore be determined with reference to the appended claims, along with the full range of equivalents to which those claims are entitled.

What is claimed is:

1. A closed loop catheter device comprising:
   an elongate, flexible catheter body having a proximal end and a distal end;
   a closed loop fluid flow circuit comprising a first lumen through which a fluid may flow into the catheter body and a second lumen through which fluid that has entered the catheter body through the first lumen may subsequently flow out of the catheter body;
   a connector on the proximal end of the catheter body, said connector having an inflow lumen which is connectable to and disconnectable from an inflow fluid source and an outflow lumen which is connectable and disconnectable from an outflow fluid receiver into which fluid may flow out of the first lumen; and,
   a valving apparatus which prevents fluid from entering one of the first and second lumens when the connector is disconnected from at least the inflow source, such that fluid may then be evacuated from the closed loop circuit through the other of the first and second lumens without concurrent entry of make-up air or other fluid into the closed loop circuit.

2. A closed loop catheter device according to claim 1 further comprising a fluid reservoir formed on or in the catheter body in communication with the first and second lumens such that fluid that flows into the catheter through the first lumen enters the reservoir and fluid that has entered the reservoir subsequently flows out of the second lumen.

3. A closed loop catheter device according to claim 2 wherein the reservoir comprises an expandable reservoir that expands when filled with fluid.

4. A closed loop catheter device according to claim 2 wherein the reservoir comprises a heat exchanger through which heat exchange fluid is circulated.

5. A closed loop catheter device according to claim 2 wherein the reservoir comprises an expandable heat exchanger which expands and contracts in response to the pressure of heat exchange fluid within the heat exchanger.

6. A closed loop catheter device according to claim 5 wherein the heat exchanger comprises a heat exchange balloon that is positioned on the catheter body, said heat exchange balloon having a deflated configuration of a first diameter and an inflated configuration of a second diameter.

7. A closed loop catheter device according to claim 6 wherein the heat exchange balloon comprises a plurality of lobes through which the heat exchange fluid circulates.

8. A closed loop catheter device according to claim 7 wherein at least some of the lobes are helically disposed about a central axis.

9. A closed loop catheter device according to claim 8 wherein the heat exchange balloon comprises central lobe and a plurality of outer lobes helically disposed about the central lobe.

10. A closed loop catheter device according to claim 4 wherein the catheter is insertable into the vasculature of a human or veterinary patient and advanceable to a position where the heat exchanger is positioned within a blood vessel whereby the heat exchanger is useable to exchange heat with blood flowing through that blood vessel.

11. A closed loop catheter device according to claim 1 further comprising a latch member for deterring inadvertent disconnection of the connector from the inflow source and outflow receiver.

12. A closed loop catheter device according to claim 1 further comprising a pressure indicator for indicating the fluid pressure within the closed loop circuit.

13. A closed loop catheter device according to claim 4 further comprising a pressure indicator for indicating the fluid pressure within the expandable reservoir.

14. A closed loop catheter device according to claim 13 wherein the expandable reservoir has a collapsed state and an expanded state and wherein the pressure indicator indicates when the pressure within the closed loop circuit is sufficiently low to cause the expandable reservoir to be in its collapsed state.

15. A closed loop catheter device according to claim 1 further comprising:
   a distal catheter hub that is affixable to a body surface of a human or veterinary patient, said distal catheter hub having a proximal end, a distal end and a hollow bore extending therethrough, the catheter body being slidably disposed within the hollow bore of the distal catheter hub such that the catheter body may be advanced through said hollow bore and into the patient's body, a generally tubular sterility barrier extending from the proximal end of the distal catheter hub and around an exteriorized portion of the catheter body to deter microbial contamination of that exteriorized portion of the catheter body.

16. A closed loop catheter device according to claim 15 further comprising:
   a proximal catheter hub affixed to the proximal end of the catheter body, said generally tubular sterility barrier having a proximal end and a distal end, the distal end of the sterility barrier being attached to the distal catheter hub and the proximal end of the sterility barrier being affixed to the proximal catheter hub, the exteriorized portion of the catheter body comprising that portion of the catheter body that is between the proximal and distal catheter hubs and within the generally tubular sterility barrier.

17. A closed loop catheter device according to claim 15 wherein the generally tubular sterility barrier is substantially transparent such that the exteriorized portion of the catheter body may be visualized through the sterility barrier.

18. A closed loop catheter device according to claim 17 wherein graduated distance markings are formed on the exteriorized portion of the catheter body so that the operator may determine the approximate length of the catheter body that has been inserted into the patient's body.

19. A closed loop catheter device according to claim 17 wherein the sterility barrier is flexible.

20. A closed loop catheter device according to claim 19 wherein the generally tubular sterility barrier is substantially formed of flexible plastic film.

21. A closed loop catheter device according to claim 1 further comprising a negative pressure apparatus connector for attaching a negative pressure apparatus to the lumen which remains open after the connector has been disconnected thereby facilitating the use of negative pressure to draw remaining fluid from the closed loop circuit.

22. A closed loop catheter device according to claim 21 wherein the negative pressure apparatus connector comprises a Luer connector which facilitates attachment of a syringe to the lumen that remains open such that the syringe may be used to draw remaining fluid from the closed circuit loop.

23. A closed loop catheter device according to claim 1 wherein the closure of the valving apparatus upon disconnection of the connector is substantially permanent so as to deter reuse of the catheter device.

24. A system for controlling the body temperature of a human or veterinary patient, said system comprising a closed loop catheter device according to claim 4, further in combination with:
   an extracorporeal heat transfer fluid vessel which serves as both the inflow fluid source and the outflow fluid receiver, said connector being connectable to and disconnectable from the extracorporeal heat transfer fluid vessel; such that heat transfer fluid may flow from the vessel;
   heater/cooler apparatus for alternately heating and cooling heat exchange fluid as it circulates through the extracorporeal heat transfer fluid vessel;
   fluid propulsion apparatus for propelling the heated or cooled heat transfer fluid from the extracorporeal heat exchange fluid vessel, through the inflow lumen of the connector, through the first lumen of the catheter, through the heat exchanger, through the second lumen of the catheter, through the outflow lumen of the connector and back into the extracorporeal heat exchange fluid vessel;
   body temperature sensing apparatus for sensing the patient's body temperature;
   a controller which receives i) a target temperature input and ii) a signal from the body temperature sensing apparatus indicating the patient's body temperature, said controller being operative to control at least one of the heater/cooler apparatus and fluid propulsion apparatus in response to at least one signal received from the body temperature sensing apparatus to raise or lower the patient's body temperature to approximately the input target temperature.

25. A system according to claim 24 wherein the heater/cooler apparatus comprises a housing, a heating/cooling element positioned within the housing and an opening through which the extracorporeal heat exchange fluid vessel may be inserted into the housing such that the heating/cooling element will heat or cool the heat transfer fluid contained within the extracorporeal heat transfer fluid vessel.

26. A system according to claim 24 comprising first and second body temperature sensors and wherein the controller receives the first and second temperature signals from the first and second body temperature sensors and determines whether the difference between the first and second temperature signals exceeds a predetermined maximum acceptable temperature difference.

27. A system according to claim 26 wherein the controller causes the system to shut down when the difference between the first and second temperature signals exceeds the predetermined maximum acceptable temperature difference.

28. A system according to claim 26 wherein the controller causes an error signal to be emitted when the difference between the first and second temperature signals exceeds the predetermined maximum acceptable temperature difference.

29. A system according to claim 26 wherein the controller selects one of the temperature signals as the driver signal if the difference between the first and the second temperature signal does not exceed a predetermined maximum amount.

30. A system according to claim 29 wherein the controller selects the higher temperature signal as the driver signal.

31. A system according to claim 29 wherein the controller selects the lower temperature signal as the driver signal.

32. A catheter device that is insertable into the body of a human or veterinary patient, said catheter device comprising:
   a flexible catheter having a distal end and a proximal end, said catheter being insertable, distal end first, into the patient's body such that a distal portion of the catheter resides within the patient's body and a proximal portion of the catheter remains exteriorized, the catheter including a closed loop fluid flow circuit comprising a first lumen through which a fluid may flow into the catheter body and a second lumen through which fluid that has entered the catheter body through the first lumen may subsequently flow out of the catheter body;
   a distal catheter hub that is affixable to a body surface of the patient, said distal catheter hub having a proximal end, a distal end and a hollow bore extending therethrough, the catheter slidably disposed within the hollow bore of the distal catheter hub, the catheter being advanceable through said hollow bore and into the patient's body such that the exteriorized proximal portion of the catheter extends out of the proximal end of the distal catheter hub;
   a proximal catheter hub on the proximal end of the catheter body; and,
   a sterility barrier configured to substantially surround the exteriorized portion of the catheter so as to substantially prevent microbial contamination of the exteriorized portion of the catheter, the sterility barrier comprising a generally tubular barrier that is affixed to and extends between the proximal catheter hub and the distal catheter hub so as to surround the exteriorized portion of the catheter.

33. A catheter device according to claim 32 wherein the sterility barrier is substantially transparent such that the exteriorized portion of the catheter body may be visualized through the sterility barrier.

34. A catheter device according to claim wherein graduated distance markings are formed on the exteriorized portion of the catheter so that the operator may determine the approximate length of the catheter body that has been inserted into the patient's body.

35. A catheter device according to claim 32 wherein the sterility barrier is flexible.

36. A catheter device according to claim 32 wherein the sterility barrier is substantially formed of flexible plastic film.

37. A catheter device according to claim 32 wherein the proximal catheter hub is also affixable to the patient's body.

38. A catheter device according to claim 32 wherein the catheter further comprises:
   a connector on the proximal end of the catheter body, said connector having an inflow lumen which is connectable to and disconnectable from an inflow fluid source and an outflow lumen which is connectable and disconnectable from an outflow fluid receiver into which fluid may flow out of the first lumen; and,
   a valving apparatus which prevents fluid from entering one of the first and second lumens when the connector is disconnected from at least the inflow source, such that fluid may then be evacuated from the closed loop circuit through the other of the first and second lumens without concurrent entry of make-up air or other fluid into the closed loop circuit.

39. A catheter device according to claim 38 further comprising a fluid reservoir formed on or in the catheter body in communication with the first and second lumens such that fluid that flows into the catheter through the first lumen enters the reservoir and fluid that has entered the reservoir subsequently flows out of the second lumen.

40. A catheter device according to claim 39 wherein the reservoir comprises an expandable reservoir that enlarges when filled with fluid.

41. A catheter device according to claim 39 wherein the reservoir comprises a heat exchanger through which heat exchange fluid is circulated.

42. A catheter device according to claim 39 wherein the reservoir comprises a heat exchanger which expands and contracts in response to the pressure of heat exchange fluid within the heat exchanger.

43. A catheter device according to claim 41 wherein the heat exchanger comprises a heat exchange balloon that is positioned on the catheter body, said heat exchange balloon having a deflated configuration of a first diameter and an inflated configuration of a second diameter.

44. A catheter device according to claim 43 wherein the heat exchange balloon comprises a plurality of lobes through which the heat exchange fluid circulates.

45. A catheter device according to claim 44 wherein at least some of the lobes are helically disposed about a central axis.

46. A catheter device according to claim 45 wherein the heat exchange balloon comprises a central lobe and a plurality of outer lobes helically disposed about the central lobe.

47. A catheter device according to claim 41 wherein the catheter is insertable into the vasculature of a human or veterinary patient and advanceable to a position where the heat exchanger is positioned within a blood vessel such that the heat exchanger is useable to exchange heat with blood flowing through that blood vessel.

48. A catheter device according to claim 38 further comprising a latch member for deterring inadvertent disconnection of the connector from the inflow source and outflow receiver.

49. A catheter device according to claim 38 further comprising a pressure indicator for indicating the fluid pressure within the closed loop circuit.

50. A catheter device according to claim 40 further comprising a pressure indicator for indicating the fluid pressure within the expandable reservoir.

51. A catheter device according to claim 50 wherein the expandable reservoir has a collapsed state and an expanded state and wherein the pressure indicator indicates when the pressure within the closed loop circuit is sufficiently low to cause the compliant reservoir to be in its collapsed state.

* * * * *